United States Patent
Cao et al.

(10) Patent No.: US 7,310,877 B2
(45) Date of Patent: Dec. 25, 2007

(54) METHOD OF PRODUCING SENSORS FOR MONITORING CORROSION OF HEAT-EXCHANGER TUBES

(75) Inventors: Jieyu Cao, Xi'an (CN); Jingxia Song, Xi'an (CN); Deliang Wang, Xi'an (CN); Guojun Long, Xi'an (CN); Benda Sun, Xi'an (CN); Jiantao Yao, Xi'an (CN); Weike Zhang, Xi'an (CN); Tao Liu, Xi'an (CN); Bing Liu, Xi'an (CN)

(73) Assignee: Thermal Power Research Institute, Xi'an (CN)

( * ) Notice: Subject to any disclaimer, the term of this patent is extended or adjusted under 35 U.S.C. 154(b) by 580 days.

(21) Appl. No.: 10/917,457

(22) Filed: Aug. 13, 2004

(65) Prior Publication Data

US 2005/0045483 A1    Mar. 3, 2005

(30) Foreign Application Priority Data

Aug. 29, 2003   (CN) .................................. 03134526

(51) Int. Cl.
*B23P 17/00* (2006.01)
*B21D 51/16* (2006.01)

(52) U.S. Cl. ............................. 29/890.031; 29/890.14; 29/401.1; 29/425

(58) Field of Classification Search ........... 29/890.031, 29/401.1, 890.14, 425
See application file for complete search history.

(56) References Cited

OTHER PUBLICATIONS

Yang, B., Corrosion Engineering, vol. 51, No. 2, pp. 153-164, (1995).
Strauss, S. D., Water Treatment.
Uchida et al., Corrosion, Paper No. 408, pp. 408/1-408/13, (1997).

*Primary Examiner*—David P. Bryant
*Assistant Examiner*—Sarang Afzali
(74) *Attorney, Agent, or Firm*—Birch, Stewart, Kolasch & Birch, LLP

(57) ABSTRACT

The present invention relates to a method of producing the sensors for monitoring corrosion of heat exchanger tubes in a thermal power plant. The sensor is made of the tubes taken out from actual heat-exchanger. As a result, the sensor not only has the same material as the actual heat-exchanger tubes, but also has the same surface state where it contacts the working medium. Therefore, a serious technical difficulties have been solved that the sensor made by the prior art can't measure different corrosion states of actual heat-exchanger tubes, that the corrosion rate measured is different from the corrosion rate of actual heat-exchanger tubes, and that the cost of anti-corrosive treatments is high . By use of the sensor made by the present invention, the different corrosion states of actual heat-exchanger tubes can be measured, not only the rate of uniform corrosion of actual heat-exchanger tubes can be measured but also the rate of localized corrosion of the heat-exchanger tubes can be measured. Moreover, the cost of treatment of anti-corrosion can be decreased.

9 Claims, 2 Drawing Sheets

METHOD OF PRODUCING SENSORS FOR MONITORING CORROSION OF HEAT-EXCHANGER TUBES

This Nonprovisional application claims priority under 35 U.S.C. §119(a) on Patent Application No(s). 03134526.3 filed in China on Aug. 29, 2003, the entire contents of which are hereby incorporated by reference.

BACKGROUND OF THE INVENTION

1. Field of the Invention

The present invention relates to a method of producing a sensor for monitoring corrosion of the heat-exchanger tubes of a heat exchanger.

2. Description of the Related Art

There are several thousand to several ten thousand of heat-exchanger tubes in a heat exchanger in a thermal power plant. For example, there are more than twenty thousand of heat-exchanger tubes in a condenser in a thermal power generating unit with power of 300 MW. In the most common cases, corrosion or severe corrosion occurs only in a relatively small number of heat-exchanger tubes, while no corrosion or slight corrosion occurs in a relatively large number of heat-exchanger tubes. Leakage resulted from corrosion of heat-exchanger tubes leads to corrosion and scaling of the boiler heating surface, explosion of the boiler tubes and accumulation of salt on a steam turbine in a thermal power plant. As a result, the direct economic losses resulting from the unplanned shutdown of the power generation units and replacing of the water walls of the boiler together with the indirect losses resulting from deterioration of the boiler and the turbine efficiency because of scaling amount up to several million RMB. In a conventional method of producing sensors for monitoring corrosion of heat-exchanger tubes, the sensors are made of the same material as that of the heat-exchanger tubes. However, the sensors made by the above conventional method have the following disadvantages:

1. As there are several thousand to several ten thousand of heat-exchanger tubes in a heat exchanger, corrosion with different degrees occurs in different heat-exchanger tubes of the heat exchanger. However, different corrosion states of the different heat-exchanger tubes can not be monitored by a conventional sensor for monitoring corrosion of heat-exchanger tubes. Especially, a conventional sensor for monitoring corrosion of heat-exchanger tubes can not measure the localized corrosion rate of a corrosion pit in which the most severe corrosion occurs.

2. The corrosion rate measured by a conventional sensor for monitoring corrosion is different from the corrosion rate of actual heat-exchanger tubes. The electrodes of a conventional sensor for monitoring corrosion are made of unused metal material which is the same as that of the heat-exchanger tubes. Although the conditions of the sensors, such as the composition of material, water quality, flow rate of water, heat load and temperature of water, can be regulated to be the same as those of actual operating heat-exchanger tubes, the surface state of sensor is different from that of the actual interior surfaces of the heat-exchanger tubes. In most cases, the corrosion of the heat-exchanger tubes mainly depends on the interior surface state of the heat-exchanger tubes. Therefore, the corrosion rate measured by a conventional sensor for monitoring corrosion is different from the corrosion rate of the actual heat-exchanger tubes.

3. The cost of anticorrosion treatments for heat-exchanger tubes is high. Considering that the thermal power generating unit operates continuously and the conventional sensors for monitoring corrosion can not measure the different corrosion states of the heat-exchanger tubes in which corrosion has occurred, it is difficult to determine whether an anticorrosion treatment is effective or not. As a result, the cost of anticorrosion treatment is high and appropriate opportunity for performing anti-corrosion treatment of the heat-exchanger tubes is easily to be missed.

SUMMARY OF THE INVENTION

The present invention has been made to overcome the above mentioned disadvantages that conventional sensors for monitoring corrosion can not monitor the different states of corrosion. Moreover, it has also been made to solve the problems that the corrosion rate measured by conventional sensors for monitoring corrosion is different from the corrosion rate of the actual heat-exchanger tubes and cost of anticorrosion treatment is high.

The above object has been accomplished by providing two new methods of producing sensors for monitoring corrosion:

1. A method of producing a sensor for monitoring uniform corrosion of heat-exchanger tubes includes the steps of:

(a) selecting and taking out heat-exchanger tubes from a heat exchanger;

(b) taking out a plurality of blanks which work as operating electrodes of the sensor from the heat-exchanger tubes;

(c) sealing cutting surfaces of the blanks with an insulating process so as to form operating electrodes of the sensor;

(d) sealing the operating electrodes with each other with an insulating process so that the operating electrodes are fixedly connected to form an integral body, thereby producing the sensor for monitoring the uniform corrosion of the heat-exchanger tubes.

Preferably, the heat-exchanger tube selected from the heat exchanger is a tube in which the most severe corrosion occurs, and said blanks are segments or short tubes taken from the heat-exchanger tube and the blanks include the portion in which the most severe corrosion occurs.

Preferably, the heat-exchanger tube selected from the heat exchanger is a tube in which the degree of corrosion is the most general in all heat-exchanger tubes, and said blanks are segments or short tubes taken from the heat-exchanger tube and the blanks include the portion in which the degree of corrosion is the most general in all heat-exchanger tubes.

Preferably, the heat-exchanger tube selected from the heat exchanger is a tube in which the slightest corrosion occurs, and said blanks are segments or short tubes taken from the heat-exchanger tube and the blanks include the portion in which the slightest corrosion occurs.

Preferably, the heat-exchanger tube selected from the heat exchanger is a tube without corrosion, and said blanks are segments or short tubes taken from the heat-exchanger tube.

Preferably, the number of the blanks is two or three or more than three, and two or three or more than three operating electrodes of the sensor are formed correspondingly.

Preferably, the step of selecting said heat-exchanger tube is any one of eddy current inspection, endoscopy, sonic detection, leakage detection by hydraulic pressure, leakage detection by foam, leakage detection by plastics thin-film, leakage detection by fluorescence and spot-check by taking out tubes.

Preferably, the process of sealing the surfaces is preformed by any one of coating, compression with insulating layer and bonding.

2. A method of producing a sensor for monitoring localized corrosion of heat-exchanger tubes includes the steps of:

(a) selecting and taking out heat-exchanger tubes from a heat exchanger;

(b) taking out several blanks which work as operating electrodes of the sensor from the heat-exchanger tubes;

(c) sealing cutting surfaces of the blanks with an insulating process so as to form operating electrodes of the sensor;

(d) sealing the operating electrodes with each other with an insulating process so that the operating electrodes are fixedly connected to form an integral body, thereby producing a sensor for monitoring the localized corrosion of the heat-exchanger tubes.

Preferably, the heat-exchanger tubes selected from the heat exchanger are the tubes with corrosion pits, and a blank taken from the heat-exchanger tubes is a segment or short tube with a corrosion pit and another blank taken from the heat-exchanger tubes is a segment or short tube with slight corrosion.

Preferably, cutting surfaces of the blank with a corrosion pit and interior surfaces of the blank except the corrosion pit are sealed with an insulating process so as to form an anode of the sensor, and cutting surfaces of the blank with slight corrosion or without corrosion pits are sealed with an insulating process so as to form a cathode of the sensor.

Preferably, the method of selecting said heat-exchanger tubes is any one of eddy current inspection, endoscopy, sonic detection, leakage detection by hydraulic pressure, leakage detection by foam, leakage detection by plastics thin-film, leakage detection by fluorescence and spot-check by taking out tubes.

Preferably, said method which is used to seal the surfaces is any one of coating, compression with insulating layer and bonding.

The method of producing the sensors for monitoring corrosion of heat exchanger tubes according to the present invention is advantageous in the following aspects:

1. The method can be used to monitor the different states of corrosion of the actual heat exchanger tubes. In the present invention, a heat exchanger tube with corrosion pits, a heat exchanger tube in which the most severe corrosion occurs, a heat exchanger tube in which the slightest corrosion occurs, and a heat exchanger tube in which the degree of corrosion is the most general in all heat-exchanger tubes are selected from a heat exchanger respectively to form sensors for monitor corrosion, therefore, the actual corrosion states of all the heat-exchanger tubes can be sensitively and reliably monitored.

2. The measured result can truly reflect the actual states of corrosion. The sensor is made of actual heat exchanger tubes and the operating surface of the sensor is kept to be same as the original surface state of the actual heat exchanger tubes. Therefore, the state of the operating surface of the sensor is same as that of the actual heat exchanger tubes. Thus, the authenticity and reliability of the result monitored by the sensors can be ensured, and the actual corrosion rate and the state of corrosion of the heat-exchanger tubes can be accurately monitored.

3. The measured result can truly reflect the actual states of localized corrosion of the heat-exchanger tubes. The anode of the sensor is made of materials selected from a portion of the heat-exchanger tubes in which the severe localized corrosion occurs, and the cathode of the sensor is made of a portion of the heat-exchanger tubes without localized corrosion. The sensor made of the above materials can accurately monitor the rate of actual localized corrosion of the heat-exchanger tubes.

4. The cost of anti-corrosion treatments is low. As the sensor made according to the present invention can quickly and accurately monitor the actual corrosion rate and corrosion state of the heat-exchanger tubes during operation in a few minutes, it is possible to detect problem of corrosion of the heat-exchanger tubes, verify effectiveness of anti-corrosion treatment of the heat-exchanger tubes and provide guidance for adjusting treatment for anti-corrosion. As a result, further corrosion damages to the heat-exchanger tubes can be prevented, and the problem of corrosion can be solved at low cost.

Additional aspects and advantages of the invention will be set forth in part in the description that follows, and in part, will be obvious from the description, or may be learned by the practice of the invention.

BRIEF DESCRIPTION OF THE DRAWINGS

The above and other objects and advantages of the invention will become apparent and readily appreciated from the following description of the preferred embodiments, taken in conjunction with the accompanying drawings, in which.

Figure 1:
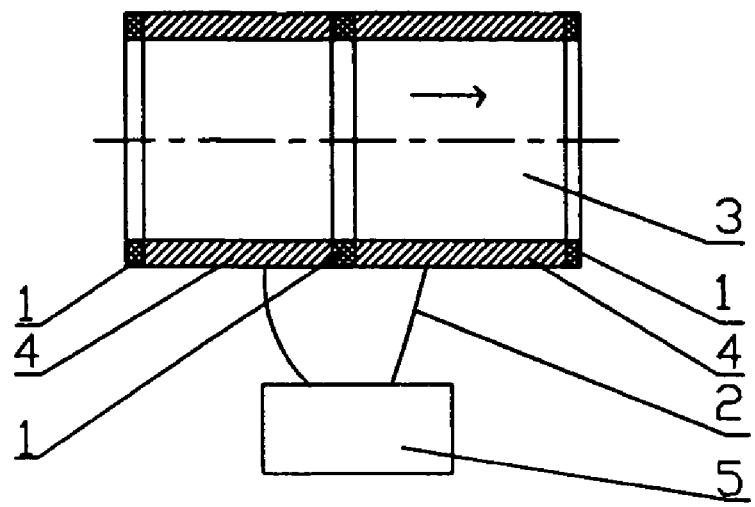
FIG. 1 is a schematic view of a sensor for monitoring uniform corrosion of heat exchanger tubes made by the method according to the present invention.

In the drawings, the reference numerals designate the following components, respectively. Reference numeral 1 designates a insulating layer; reference numeral 2 designates a lead wire; reference numeral 3 designates a sensor for monitoring uniform corrosion; reference numeral 4 designates operating electrodes of a sensor for monitoring uniform corrosion; reference numeral 5 designates an apparatus for monitoring uniform corrosion; reference numeral 6 designates a sensor for monitoring localized corrosion; reference numeral 7 designates a cathode of a sensor for monitoring localized corrosion; reference numeral 8 designates an anode of a sensor for monitoring localized corrosion; reference numeral 9 designates a corrosion pit; reference numeral 10 designates an apparatus for monitoring localized corrosion; reference numeral 11 designates the heat-exchanger tubes of a heat exchanger; reference numeral 12 designates a valve on a water inlet port of the monitoring loop; reference numeral 13 designates a valve on a water outlet port of the monitoring loop; reference numeral 14 designates water returning chamber of the heat exchanger; reference numeral 15 designates water inlet chamber of the heat exchanger; reference numeral 16 designates water outlet chamber of the heat exchanger; reference numeral 17 designates an outlet tube of cooling water of the heat exchanger; and reference numeral 18 designates an inlet tube of cooling water of the heat exchanger.

DETAILED DESCRIPTION OF THE PREFERRED EMBODIMENTS

A preferred embodiment of the present invention will be described hereinafter in detail with reference to the attached drawings. The present invention may, however, be embodied in many different forms and should not be construed as being limited to the embodiment set forth herein; rather, this embodiment is provided so that the present disclosure will be thorough and complete, and will fully convey the concept of the invention to those skilled in the art.

Referring to FIG. 1, a method of producing a sensor for monitoring uniform corrosion rate of heat exchanger tubes includes the following steps:

1. selecting a heat exchanger tube in which the degree of corrosion is the most general in all heat-exchanger tubes from a heat exchanger by eddy current inspection and taking out the tube;

2. taking out three tubular blanks from said heat exchanger tube;

3. sealing cutting surfaces of said three blanks with an insulating process and separating the exterior surfaces of the blanks from working medium, and the interior surfaces of the blanks works as surfaces of operating electrodes of the sensor;

4. sealing the three operating electrodes with each other with an insulating process so that the operating electrodes are fixedly connected to form an integral body, thereby producing a sensor for monitoring uniform corrosion of the heat-exchanger tubes.

A method of producing another sensor for monitoring uniform corrosion of the heat-exchanger tubes includes the following steps:

1. selecting a heat exchanger tube in which the most severe corrosion occurs from a heat exchanger by eddy current inspection and taking out the tube;

2. taking out two blanks including the portion in which the most severe corrosion occurs from the heat-exchanger tube;

3. sealing the cutting surfaces of the blanks with an insulating process, embedding said two blanks on a wall of said two insulating tubes so as to form two operating electrodes and separate exterior surfaces of the blanks from working medium while the interior surfaces of the blanks contact with said working medium, and the interior surfaces of the blanks work as surfaces of operating electrodes of the sensor;

4. sealing the two operating electrodes with each other with an insulating process so that the operating electrodes are fixedly connected to form an integral body, thereby producing a sensor for monitoring uniform corrosion of the heat-exchanger tubes.

Figure 2:
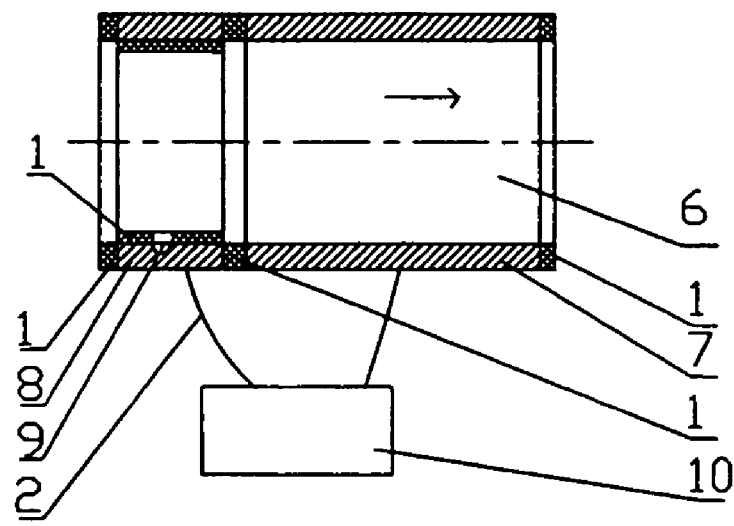
FIG. 2 is a schematic view of a sensor for monitoring localized corrosion of heat exchanger tubes made by the method according to the present invention.

Referring to FIG. 2, a method of producing a sensor for monitoring localized corrosion rate of the heat-exchanger tubes according to the present invention includes the following steps:

1. selecting a heat exchanger tube with corrosion pits from a heat exchanger by eddy current inspection and taking out the tube;

2. taking out a tubular blank with a corrosion pit from the tube and a tubular blank without corrosion pit or with a corrosion mark lighter than the corrosion pit from the tube;

3. sealing cutting surfaces of the blank with a corrosion pit and the interior surfaces except the corrosion pit with an insulating process so as to form an anode of the sensor, wherein the corrosion pit works as the surface of an anode of the sensor; and sealing the cutting surfaces of the blanks without corrosion pit or with a corrosion mark lighter than the corrosion pit with an insulating process so as to form a cathode of the sensor, wherein interior surfaces work as surfaces of cathode of the sensor;

4. sealing the cathode and the anode of the sensor with each other with an insulating process so that the cathode and the anode are fixedly connected to form an integral body, thereby producing a sensor for monitoring localized corrosion rate of the heat-exchanger tubes.

A method of producing a sensor for monitoring the localized corrosion rate of the heat-exchanger tubes according to the present invention includes the following steps:

1. selecting a heat exchanger tube with corrosion pits from a heat exchanger by eddy current inspection and taking out the tube;

2. taking out a segment with a corrosion pit as a blank and a tubular blank without corrosion pit or with a corrosion mark lighter than the corrosion pit from the tube;

3. sealing cutting surfaces of the blank with a corrosion pit and the interior surfaces except the corrosion pit with an insulating process, then embedding said blank with a corrosion pit on a wall of the insulating tube so as to form an anode of the sensor, wherein the corrosion pit works as the surface of the anode of the sensor; and sealing cutting surfaces of the blanks without corrosion pit or with a corrosion mark lighter than the corrosion pit with an insulating process so as to form a cathode of the sensor, wherein the interior surfaces works as the surface of the cathode of the sensor;

4. sealing the cathode and the anode with each other with an insulating process so that the cathode and the anode are fixedly connected to form an integral body, thereby producing a sensor for monitoring the localized corrosion rate of the heat exchanger tubes.

The principle of the present invention will be described in detail as follows.

Although the conditions of all heat-exchanger tubes in a heat-exchanger, such as the composition of material, water quality, flow rate of water, heat load and water temperature are substantially same, generally corrosion or severe corrosion occurs in a small number of heat-exchanger tubes, but a relatively large number of heat-exchanger tubes are not corroded or are corroded slightly. In fact, the occurrence of corrosion mainly depends on the surface state of heat-exchanger tubes, if there are some abnormal substance (such as carbon residues, inclusion, deposits, scale or biofilm et al) attached on the surface of heat-exchanger tubes, corrosion is likely to occur.

When corrosion occurs in the heat-exchanger tubes, inhibitor can be injected into the loop of the heat exchanger to control the corrosion. However, it is difficult for inhibitor to reach the bottom of the corrosion pit of the heat-exchanger tubes because the corrosion pit is covered by corrosion product. Furthermore the corrosion leads to partial acidification, lack of oxygen and increase in concentration of corrosive ions in the corroded portion. Therefore, the quantity of inhibitor used to control the corrosion in the most severely corroded portion of heat exchanger tube is larger than that for the other portion of the heat exchanger tube. Therefore, if the most severe corrosion of heat-exchanger tubes can be effectively controlled, the corrosion of heat exchanger tubes with slight corrosion or no corrosion is bound to be effectively controlled.

According to the principle of electrochemical corrosion, a rapid anode dissolution occurs due to increase of partial anion concentration, lack of oxygen, decrease of pH at the bottom of the corrosion pit. The lost electrons flow toward the surface of the heat exchanger tube surrounding a corrosion pit through the body of the heat exchanger tube. Accordingly, the surface surrounding the corrosion pit of the heat exchanger tube works as a cathode and the reduction of oxygen takes place. If the current flowing from the bottom of the corrosion pit to the surrounding portion can be measured, the corrosion rate of the corrosion pit can be quantitatively calculated. For this purpose, a heat exchanger tube having a corrosion pit is selected and a portion of heat exchanger tube with a corrosion pit is cut out. Then, the metal surface surrounding the corrosion pit is sealed with an insulating process so that only the corrosion pit is exposed. In the way, a galvanic couple is constituted by this cut-out portion and another part of the tube without corrosion pits. Thereafter, the current flowing through the galvanic couple is measured, and the corrosion rate of the corrosion pit can be calculated. The sensor for monitoring corrosion made by this method can be used to monitor the corrosion rate of the corrosion pit. Then, according to the results, anti-corrosive treatments can be adjusted. For example, different inhibitors can be used and the quantity of the inhibitor can be adjusted until the corrosion rate of the corrosion pit decreases significantly or reaches a safety value.

Likewise, a heat exchanger tube in which the most severe corrosion occurs, a heat exchanger tube in which the slightest corrosion occurs and a heat exchanger tube in which degree of corrosion is the most general in all heat-exchanger tubes are taken out from the heat exchanger to produce several sensors for monitoring uniform corrosion respectively so as to simulate the different corrosion states of the heat-exchanger tubes. When an inhibitor is added into the loop of the heat-exchanger, if the most severe corrosion of the heat-exchanger tubes is effectively controlled, it shows that the corrosion of all heat-exchanger tubes in the heat exchanger is effectively controlled. If the most severe corrosion of the heat-exchanger tubes isn't effectively controlled while the corrosion of the heat-exchanger tubes in which degree of corrosion is the most general in all heat-exchanger tubes is effectively controlled, it shows that the corrosion of most of the heat-exchanger tubes is effectively controlled except few heat-exchanger tubes in which the most severe corrosion occurs. As a result, the actual corrosion states of all heat-exchanger tubes (several ten thousand of heat-exchanger tubes) of the heat-exchanger are accurately reflected by several sensors with different corrosion states. The sensors are made of the tube taken out from actual heat-exchanger. As a result ,the sensors not only have the same material as the actual heat-exchanger tube, but also have the same surface state where they contact the working medium. Therefore, the measured corrosion rate by the sensors is consistent with the corrosion rate of actual heat-exchanger tubes and reflects the different corrosion states of actual heat-exchanger tubes.

The present invention can be applied to a heat exchanger made of copper, brass, alloy of nickel and copper, stainless steel and carbon steel etc. Also, it can be applied to a heat exchanger in which freshwater or seawater or other chemical medium can be used as working medium.

The sensors made of the tubes taken from the actual heat exchanger by the present invention can be connected in series or in parallel to the monitoring circuit outside of the heat exchangers. Alternatively, the sensors can be connected in series to the circulating loop inside the heat exchanger. Additionally, a heating and temperature-controlling system can be mounted on the sensor so as to simulate the heat load of the heat-exchanger tubes.

Figure 3:
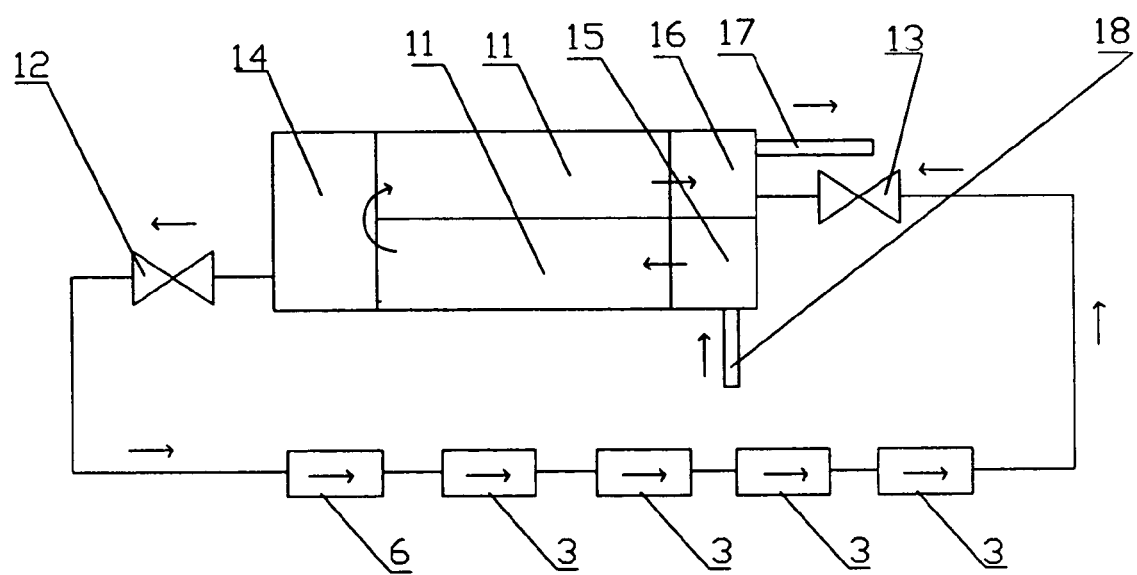
FIG. 3 is schematic view showing a monitoring method using the sensors for monitoring corrosion of heat exchanger tubes according to the present invention.

Referring to FIG. 3, a method for monitoring corrosion of heat exchanger tubes by using the sensors which is made by the present invention includes the following steps:

selecting and taking out a predetermined number of the tubes from the heat-exchanger tubes in which the most severe corrosion occurs, the slightest corrosion occurs and degree of corrosion is the most general in all heat-exchanger tubes and no corrosion occurs, and producing the sensors for monitoring uniform corrosion according to the above mentioned method; selecting and taking out a heat exchanger tube with corrosion pit and producing the sensors for monitoring localized corrosion according to the above mentioned method.

connecting the sensor for monitoring uniform corrosion and the sensor for monitoring localized corrosion in the circulating loop of the heat exchanger, while exterior surfaces of the sensor being not contacting with working medium;

connecting operating electrodes of the sensor for monitoring uniform corrosion to an apparatus for monitoring uniform corrosion through lead wires, connecting the cathode and anode of the sensor for monitoring localized corrosion to an apparatus for monitoring localized corrosion through lead wires; wherein the apparatus for monitoring localized corrosion can be selected from group consisting of: a galvanic couple meter, a zero resistance ammeter, a potentiostat, an ammeter with low resistance or eddy current detector, and wherein the apparatus for monitoring uniform corrosion can be selected from the group consisting of: a linear polarization resistance apparatus, a weak polarization apparatus, an electrochemical impedance spectroscopy apparatus, a potentiostat, a corrosion apparatus charging under constant current, a photoelectric corrosion apparatus and an electrochemical corrosion apparatus.

What is claimed is:

1. A method of producing a sensor for monitoring corrosion of a heat-exchanger tube, comprising the steps of:
    (a) selecting and taking out a plurality of heat-exchanger tubes from a heat exchanger;
    (b) cutting out a plurality of blanks which work as operating electrodes of the sensor from each one of said heat-exchanger tubes;
    (c) sealing cutoff surfaces of said blanks with an insulating process so as to form the operating electrodes of the sensor; and
    (d) sealing the operating electrodes of two adjacent blanks to each other with the insulating process so that the operating electrodes are fixedly connected to form an integral body, thereby producing the sensor for monitoring corrosion of the heat-exchanger tubes.

2. A method of producing a sensor for monitoring corrosion of the heat-exchanger tubes according to claim 1, wherein:
    said heat-exchanger tubes selected from the are the tubes in which a most severe corrosion occurs, and said blanks taken from said heat-exchanger tubes are segments or short tubes each having a portion in which the most severe corrosion occurs.

3. A method of producing a sensor for monitoring corrosion of heat-exchanger tubes according to claim 1, wherein:
    said heat-exchanger tubes selected from the heat exchanger are the tubes in which a degree of corrosion is a most general in all heat-exchanger tubes, and said blanks taken from said heat-exchanger tubes are segments or short tubes each having a portion in which the degree of corrosion is the most general in all heat-exchanger tubes.

4. A method of producing a sensor for monitoring corrosion of heat-exchanger tubes according to claim 1, wherein:
    said heat-exchanger tubes selected from the heat exchanger are the tubes in which a slightest corrosion occurs, and said blanks taken from said heat-exchanger tubes are segments or short tubes each having a portion in which the slightest corrosion occurs.

5. A method of producing a sensor for monitoring corrosion of heat-exchanger tubes according to claim 1, wherein:
said heat-exchanger tubes selected from the heat exchanger are the tubes without the corrosion, and said blanks taken from said exchanger tubes are segments or short tubes without the corrosion.

6. A method of producing a sensor for monitoring corrosion of heat-exchanger tubes according to any one of claims 2-5, wherein:
the number of said blanks is two or more, and two or more operating electrodes of the sensor are formed correspondingly.

7. A method of producing a sensor for monitoring corrosion of heat-exchanger tubes according to claim 1, wherein:
said heat-exchanger tubes selected from the heat exchanger are the tubes with corrosion pits, and said blanks taken from said heat-exchanger tubes are segments or short tubes, and there is a corrosion pit on one of said blanks and there is no corrosion or slight corrosion on other ones of said blanks.

8. A method of producing a sensor for monitoring corrosion of heat-exchanger tubes according to claim 7, wherein:
cutting surfaces of the blanks with the corrosion pit and interior surfaces except the corrosion pit are sealed with the insulating process so as to form an anode of the sensor, and cutting surfaces of the blank with the no corrosion pit or the slight corrosion are sealed with the insulating process so as to form a cathode of the sensor.

9. A method of producing a sensor for monitoring corrosion of heat-exchanger tubes according to any one of claims 1-5 and 7-8, wherein:
the step of selecting said heat-exchanger tubes is performed by any one of eddy current inspection, endoscopy, sonic detection, leakage detection by hydraulic pressure, leakage detection by foam, leakage detection by plastics thin-film, leakage detection by fluorescence or spot-check by taking out tubes.

* * * * *